United States Patent [19]
Anderson et al.

[11] Patent Number: 6,162,922
[45] Date of Patent: Dec. 19, 2000

[54] METHOD FOR PREPARING N-SUBSTITUTED HETEROCYCLIC DERIVATIVES USING A PHASE-TRANSFER CATALYST

[75] Inventors: Neal G. Anderson, Stockton; Rajendra P. Deshpande, Neshanic Station; Jerome L. Moniot, Chester, all of N.J.

[73] Assignee: Bristol-Myers Squibb Co., Princeton, N.J.

[21] Appl. No.: 09/233,238

[22] Filed: Jan. 19, 1999

Related U.S. Application Data

[60] Provisional application No. 60/073,103, Jan. 30, 1998.
[51] Int. Cl.$^7$ .................................................. C07D 235/02
[52] U.S. Cl. ............................................................. 548/300.7
[58] Field of Search ........................................... 548/300.7

[56] References Cited

U.S. PATENT DOCUMENTS 5,270,317  12/1993  Bernhart et al. .
5,288,895  2/1994  Bouisset et al. .
5,352,788  10/1994  Bernhart et al. .
5,559,233  9/1996  Bernhart et al. .

FOREIGN PATENT DOCUMENTS 475898  3/1992  European Pat. Off. .
WO 91/14679  10/1991  WIPO .

OTHER PUBLICATIONS

Pedregal et al., *J. Heterocyclic Chem.*, 21, 477 (1984).

*Primary Examiner*—Patricia L. Morris
*Attorney, Agent, or Firm*—Suzanne E. Babajko; Ronald S. Hermenau

[57] ABSTRACT

Disclosed is a process for preparing N-substituted heterocyclic derivatives and its salts using phase transfer catalysis.

11 Claims, No Drawings

METHOD FOR PREPARING N-SUBSTITUTED HETEROCYCLIC DERIVATIVES USING A PHASE-TRANSFER CATALYST

This application claims priority from provisional U.S. application Ser. No. 60/073,103, filed Jan. 30, 1998, incorporated herein by reference in its entirety.

BACKGROUND OF THE INVENTION

The present invention is directed to a process for preparing N-substituted heterocyclic derivatives 4'-[[2-alkyl or alkoxy-4-oxo-1,3-diazaspiro[4.4]non-1-en-3-yl]methyl][1,1'-biphenyl]-2-carbonitrile and its salts using phase transfer catalysis. These compounds are important intermediates in the synthesis of the final compounds 2-alkyl or alkoxy-3-[[2'-(1H-tetrazol-5-yl)[1,1'-biphenyl]-4-yl]methyl ]-1,3-diazaspiro[4.4]non-1-en-4-one and its salts which are useful as antagonists of the peptide hormone Angiotensin II.

Angiotensin II is a peptide hormone of the formula H-Asp-Arg-Val-Tyr-Ile-His-Pro-Phe-OH.

Angiotensin II is a potent vasopressor and the biologically active product of the renin-angiotensin system. Renin acts on the angiotensinogen of the plasma to produce angiotensin I, which is converted to angiotensin II by the action of the angiotensin I converting enzyme. The final compounds inhibit the action of angiotensin II on its receptors and thus prevents the increase in blood pressure produced by the hormone-receptor interaction. Thus, they are therefore useful in the treatment of hypertension and heart failure.

The preferred intermediate is 4'-[[2-butyl-4-oxo-1,3-diazaspiro [4.4]non-1-en-3-yl]methyl][1,1'-biphenyl]-2-carbonitrile which is useful in the synthesis of the final compound 2-butyl-3-[[2'-(1H-tetrazol-5-yl)[1,1'-biphenyl]-4-yl]methyl]-1,3-diazaspiro[4.4]non-1-en-4-one known by the trademark (Irbesartan) and can be easily converted to Irbesartan and its salts according to the process described in U.S. Pat. No. 5,270,317. The compound Irbesartan antagonizes the action of angiotensin II.

A synthetic route for the preparation of N-substituted heterocyclic derivatives has been described in U.S. Pat. No. 5,270,317. The process of U.S. Pat. No. 5,270,317 involves reacting a heterocyclic compound of the formula

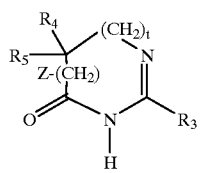

with a (biphenyl-4-yl)methyl derivative of the formula

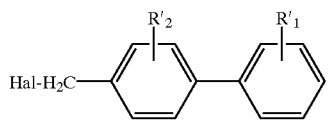

wherein $R_1$, $R_2$, $R_3$, $R_4$, $R_5$, and t, z and Hal have the meanings given in said U.S. Pat. No. 5,270,317, in the presence of an inert solvent such as DMF, DMSO or THF, with a basic reagent, for example KOH, a metal alcoholate, a metal hydride, calcium carbonate or triethylamine. The products of the reaction were purified by chromatography.

U.S. Pat. Nos. 5,352,788, and 5,559,233, and WO 91/14679 also describe identical alkylation of the nitrogen atom of the heterocyclic compound with the halo-biphenyl compound using the same inert solvent and the same basic reagents.

Also EP0 475,898 describes the alkylation of the nitrogen atom of the heterocycle of the formula

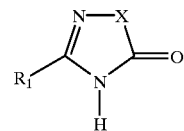

with a compound of the formula

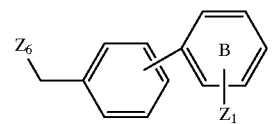

wherein X, $R_1$, $Z_1$ and $Z_6$ have the meanings given therein, in the presence of N,N-dimethylformamide and a basic reagent, such as alkalimetalhydrides for example sodium or potassium hydride.

All of the above identified patents describe alkylation in solvents, such as N,N-dimethylformamide or DMSO, etc. in the presence of a basic reagent, for example, a metal hydride or a metal alcoholate etc. The strong bases, such as metal hydride or a metal alcoholate require anhydrous reaction conditions. Since N,N-dimethylformamide is used as a solvent, its removal requires high temperature concentration by distillation, which can result in degradation of the final product. None of these patents describe alkylation using a phase transfer catalysis.

The Journal of Heterocyclic chemistry, 21 477–480, 1984 describes alkylation of hydantoins using a phase-transfer catalysis. The hydantoins are by their electronic nature more acidic than the 2-butyl-1,3-diazaspiro[4.4]nonan-4-one, hydrochloride of the present invention and therefore, there is structural divergence between the two compounds.

SUMMARY OF THE INVENTION

The object of the present invention is the provision of a process for the preparation of N-substituted heterocyclic derivative 4'-[[2-alkyl or alkoxy-4-oxo-1,3-diazaspiro[4.4] non-1-en-3-yl]methyl][1,1'-biphenyl]-2-carbonitrile and its salts using a phase transfer catalyst.

Briefly, therefore, the present invention is directed to a process for the preparation of 4'-[[2-alkyl or alkoxy-4-oxo-1,3-diazaspiro[4.4]non-1-en-3-yl]methyl][1,1'-biphenyl]-2-carbonitrile and its salts an intermediate of the formula I

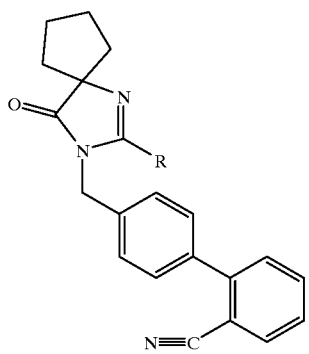

(I)

comprising reacting a 2-alkyl or alkoxy-1,3-diazaspiro[4.4]nonan-4-one hydrochloride of the formula II

(II)

with a 4'-(halomethyl)[1,1'-biphenyl]-2-carbonitrile in the presence of a phase transfer catalyst. This process is also sutable for the large scale preparation of the intermediate of formula I. The substituent R is lower alkyl or lower alkoxy and the halogen is chlorine, bromine or iodine.

DETAILED DESCRIPTION

The present invention is directed to a process for preparing a 4'-[[2-alkyl or alkoxy-4-oxo-1,3-diazaspiro[4.4]non-1-en-3-yl]methyl][1,1'-biphenyl]-2-carbonitrile and its salts, an intermediate having the following structural formula I:

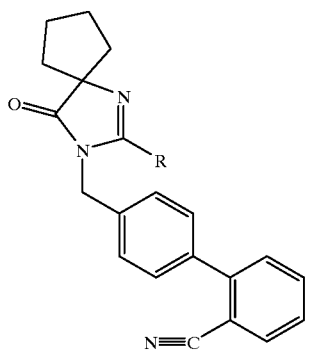

(I)

comprising reacting a 2-R-1,3-diazaspiro[4.4]nonan-4-one hydrochloride of the formula II

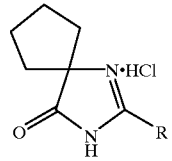

(II)

with a 4'-(halomethyl)[1,1'-biphenyl]-2-carbonitrile of the formula III

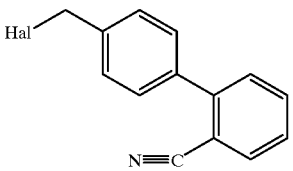

(III)

in the presence of a phase-transfer catalyst. The substituent R is lower alkyl of 1–4 carbon atoms or lower alkoxy of 1–3 carbon atoms. The lower alkyl of 1–4 carbon atoms is methyl, ethyl, n-propyl or n-butyl. The lower alkoxy of 1–3 carbon atoms is methoxy, ethoxy or n-propoxy. The preferred lower alkyl is n-butyl and the preferred lower alkoxy is n-propoxy. The hal is chlorine, bromine or iodine. The preferred halogen atom is bromine. The salts of the compound of formula I or Irbesartan are pharmaceutically acceptable salts such as the hydrochloride, the hydrobromide, the sulfate or the hydrogen sulfate.

Thus, in accordance with the process of the present invention, the alkylation of the nitrogen atom at the 1-position of the 2-R-1,3-diazaspiro[4.4]nonan-4-one hydrochloride is carried out using phase-transfer catalysis. Under the conditions of the phase-transfer catalysis, the substrates 2-R-1,3-diazaspiro[4.4]nonan-4-one hydrochloride of the formula II and 4'-(halomethyl)[1,1'-biphenyl]-2-carbonitrile of formula III are allowed to react, with vigorous stirring in a volatile, water-immiscible organic solvent in the presence of a catalytic amount of a phase transfer agent and an aqueous solution of standard inorganic bases. The reaction proceeds at ambient temperature and pressure for two to three hours. After that the reaction mixture is diluted with water, if initially less water is present or when more water is present initially, then it is not necessary to dilute the reaction mixture with water. The two phases, that is organic and aqueous, are separated and the organic phase is washed twice with water. Then the organic phase is optionally dried over sodium sulfate, filtered and evaporated to dryness under reduced pressure to an oily residue. The oily residue is crystallized from an organic solvent to give the final product. The final product can be converted into its salt by methods known in the prior art.

The organic solvent can be any water-immiscible solvent, for example, dichloromethane or toluene and the standard inorganic bases can be aqueous sodium hydroxide or potassium hydroxide. The phase-transfer catalyst is, for example, methyl tributylammonium chloride but can be any phase-transfer catalyst. The crystallization solvent can be any organic solvent that helps crystallization, such as methyl-tert-butyl-ether.

The starting materials are readily available or can be prepared by methods known in the literature including the aforementioned patents.

A preferred embodiment of the process comprises reacting a 2-butyl-1,3-diazaspiro[4.4]nonan-4-one hydrochloride and 4'-(bromomethyl)[1,1'-biphenyl]-2-carbonitrile in a water-immiscible organic solvent such as dichloromethane or toluene, in the presence of methyl-tributylammonium chloride and aqueous sodium or potassium hydroxide, separating the organic phase of dichloromethane or toluene, washing the separated organic phase with water, optionally drying the organic phase over a desiccant, filtering the organic phase, evaporating the organic phase to an oily residue and finally crystallizing the oily residue from an organic solvent, such as methyl tert butyl ether to give 4'-[[2-butyl-4-oxo-1,3-diazaspiro[4.4]non-1-en-3yl]methyl][1,1'-biphenyl]-2-carbonitrile. This compound is an intermediate in the synthesis of the compound 2-butyl-3-[[2'-(1H-tetrazol-5-yl)[1,1'-biphenyl]-4-yl]methyl]-1,3-diazaspiro[4.4]non-1-en-4-one known by the trademark (Irbesartan) and can be easily converted to Irbesartan and its salts according to the process described in U.S. Pat. No. 5,270,317. The compound Irbesartan antagonizes the action of angiotensin II.

Thus, N-alkylation by phase-transfer catalysis according to the present process provides conditions that are superior and advantageous than those described in the prior art for N-alkylation without the phase-transfer catalysis. In the present process, there is no need for chromatography and the final product is readily isolated by crystallization. Moreover, no special handling details are required in he present process, since no sodium hydride or sodium or potassium ethoxide is used. In addition the reaction time in the present process is of short duration and consequently results in increased productivity. The following examples illustrate the invention.

EXAMPLE 1

Preparation of 4'-[[2-butyl-4-oxo-1,3-diazaspiro[4.4]non-1-en-3-yl]methyl][1,1'-biphenyl]-2-carbonitrile Alkylation in toluene—50% NaOH.

A mixture of 0.231 g (1.0 mmol) of 2-butyl-1,3-diazaspiro[4.4]nonan-4-one, hydrochloride, 0.272 g (1.0 mmol) of 4'-(bromomethyl)[1,1'-biphenyl]-2-carbonitrile, 24.4 μL (0.075 mmol) of 75% aqueous solution of methyl-tributylammonium chloride, 2.0 mL of toluene and 2.0 mL of 50% aqueous solution of sodium hydroxide was vigorously stirred at room temperature for 2.2 hours. Then the reaction mixture was diluted with 2 mL of water and the two phases separated. The organic phase was extracted twice with 2 mL of water, evaporated under vacuum to give 0.33 g (85.7%) of the title compound.

1H-NMR: d (delta) 7.8–7.2 (m, 8H); 4.8 (s, 2H); 2.4 (m, 2H); 2.0 (m, 8H); 1.6 (m, 2H); 1.35 (m, 2H); 0.9 (t, 3H).

13C-NMR: d (delta) 186.7, 161.4, 144.6, 137.5, 137.1, 132.8, 129.9, 129.3 128.9, 128.1, 127.7, 127.0, 125.1, 118.5, 111.0, 76.5, 43.2, 37.3, 28.7, 27.7, 26.0, 22.2, 13.6.

EXAMPLE 2

Preparation of 4'-[[2-butyl-4-oxo-1,3-diazaspiro[4.4]non-1-en-3-yl]methyl][1,1'-biphenyl]-2-carbonitrile Alkylation in Dichloromethane—33% NaOH A mixture of 37 g, (160 mmoles) of 2-butyl-1,3-diazaspiro [4.4]nonan-4-one, hydrochloride, 1.7 mL of a 75% aqueous solution of methyl tributylammonium chloride, 125 mL of a 33% (10 N) aqueous solution of sodium hydroxide and 125 mL of methylene chloride was vigorously stirred at room temperature for five minutes. To this vigorously stirred mixture was added a solution of 44.34 g (163.6 mmoles as determined quantitatively by HPLC) of 4'-(bromomethyl) [1,1'-biphenyl]-2-carbonitrile in 400 mL of methylene chloride over a period of 40 to 60 minutes. After that, the phases were separated and the organic phase was washed twice with 100 mL of water. Then the organic phase was evaporated under reduced pressure to give an oily residue. The oily residue was dissolved in 250 mL of methyl-tertiarybutyl ether and the resulting solution was treated with 110 mL of concentrated HCl at a temperature below 40° C. Then the biphasic mixture was stirred for 10 minutes, allowed to settle and the phases separated. The aqueous acidic phase was washed once with 150 mL of methyl-tertiarybutyl ether. Then the aqueous acidic phase was divided into two equal portions and one portion was used for crystallization. To one stirred portion were added 25 mL of DMF and 25 mL of methyl-tertiarybutyl ether and 55 mL of 33% aqueous sodium hydroxide over a period of two to three hours. The slurry was allowed to stir overnight and then a total of 50 mL of water was added to the slurry and the slurry additionally stirred for 45 minutes. After that the slurry was cooled to 0° C. in an ice bath for 35 minutes and filtered. The wet cake remaining on the filter paper was washed once with a mixture of 90 mL/10 mL of water and methyl-tertiarybutyl ether. Then the cake was dried in a vacuum oven at 40° C. and at pressure of 2.3 mm Hg to give 23.3 g (yield 75.4%) of the title compound having a laboratory HPLC of HI of 99.8.

EXAMPLE 3

Preparation of 4'-[[2-butyl-4-oxo-1,3-diazaspiro[4.4]non-1-en-3-yl]methyl][1,1'-biphenyl]-2-carbonitrile Alkylation in Dichloromethane—33% NaOH A mixture of 28.9 g (125 mmoles) of 2-butyl-1,3-diazaspiro[4.4]nonan-4-one, hydrochloride, 1.3 mL of 75% aqueous solution of methyl tributylammonium chloride, 90 mL (10 N) of 33% aqueous sodium hydroxide and 90 mL of methylene chloride was vigorously stirred for 5 minutes at room temperature and then cooled to 7–12° C. To this vigorously stirred cooled mixture at 7–12° C. was added a solution of 36.04 g (132 mmoles, amount determined quantitatively by HPLC) in 300 mL of methylene chloride of 4'-(bromomethyl)[1,1'-biphenyl]-2-carbonitrile over a period of 70 minutes. After that, the reaction mixture was allowed to warm up to room temperature and stirred additionally at room temperature for a half hour. Then the phases were separated and the organic phase was washed twice with 90 mL of water. The organic phase was concentrated under reduced pressure to the minimum agitation volume, and methyl tertiarybutyl ether was added. Concentration was continued to displace the dichloromethane, and the product was crystallized from the methyl tertiarybutyl ether solution. The crystals were collected on a filter, washed with cold 120 ml of methyl-tertiarybutyl ether and dried in a vacuum oven at 40° C. and a pressure of 3.1 mm Hg to give 39.9 g (82.4%) of the title compound having a laboratory HPLC of HI 99.8.

What is claimed is:

1. A process for the preparation of a compound of formula I or its salt

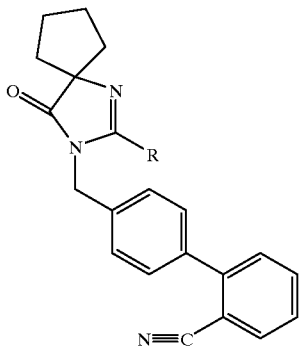

(I)

wherein R is lower alkyl of 1–4 carbon atoms or lower alkoxy of 1–3 carbon atoms, comprising the steps of:

reacting a 2-R-1-3-diazaspiro[4.4]nonan-4-one hydrochloride of formula II

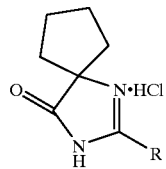

(II)

wherein R has the meaning given above, with a 4'(halomethyl)[1,1'-biphenyl]-2-carbonitrile of formula III

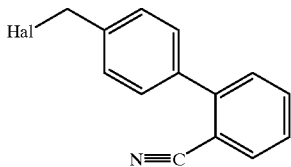

(III)

wherein Hal is chlorine, bromine or iodine, in a water-immiscible organic solvent, in the presence of an inorganic base and a phase transfer catalyst selected from quaternary onium salts, cyclic polyethers, open chain polyethers, N-alkylphosphoramides and methylene-bridged phosphorous and sulfur oxides, separating the organic solvent, optionally drying the organic solvent, filtering the organic solvent, evaporating the filtered organic solvent to give the compound of the formula I, crystallizing the compound of the formula I from an organic solvent and optionally converting the compound of formula I into its salt.

2. The process of claim 1, wherein R is methyl, ethyl, n-propyl, n-butyl, methoxy, ethoxy or propoxy and hal is bromine.

3. The process of claim 1, wherein R is n-butyl or propoxy and hal is bromine.

4. The process of claim 1, wherein the water-immiscible organic solvent is methylene chloride or toluene and the inorganic base is sodium hydroxide or potassium hydroxide.

5. The process of claim 1, wherein the phase-transfer catalyst is methyl tributylammonium chloride.

6. The process of claim 1, wherein the reaction is carried out at room temperature.

7. The process of claim 1 wherein the compound of formula I is crystallized from methyl-tertiarybutyl ether.

8. The process of claim 1, wherein the salt is hydrochloride, hydrobromide or hydrogen sulfate.

9. A process for the preparation of 4'-[[2-butyl-4-oxo-1,3-diazaspiro[4.4]non-1-en-3-yl]methyl][1,1'-biphenyl]-2-carbonitrile or its salt comprising the steps of, reacting a 2-butyl-1,3-diazaspiro [4.4]nonan-4-one hydrochloride with a 4'-(bromomethyl)[1,1'-biphenyl]-2-carbonitrile in a water-immiscible organic solvent, in the presence of an inorganic base and a phase transfer catalyst selected from quaternary onium salts, cyclic polyethers, open chain polyethers, N-alkylphosphoramides and methylene-bridged phosphorous and sulfur oxides, separating the organic solvent, optionally drying the organic solvent, filtering the organic solvent, evaporating the filtered organic solvent to give an oily product, crystallizing the oily product from an organic solvent to give 4'-[[2-butyl-4-oxo-1,3-diazaspiro[4.4]non-1-en-3-yl]methyl][1,1'biphenyl]-2-carbonitrile and optionally converting it into its salt.

10. The process of claim 9, wherein the salt is a hydrochloride, hydrogen bromide or hydrogen sulfate.

11. The process of claim 1, wherein the phase transfer catalyst is a quaternary onium salt.

* * * * *